United States Patent [19]

Vorbrueggen

[11] 4,140,853
[45] Feb. 20, 1979

[54] PROCESS FOR THE PREPARATION OF AMINOPYRIDINES

[75] Inventor: Helmut Vorbrueggen, Berlin, Fed. Rep. of Germany

[73] Assignee: Schering Aktiengesellschaft, Berlin and Bergkamen, Fed. Rep. of Germany

[21] Appl. No.: 858,330

[22] Filed: Dec. 6, 1977

Related U.S. Application Data

[63] Continuation of Ser. No. 677,819, Apr. 16, 1976, abandoned.

[30] Foreign Application Priority Data

Apr. 18, 1975 [DE] Fed. Rep. of Germany ....... 2517774

[51] Int. Cl.² .................. C07D 213/73; C07D 213/74
[52] U.S. Cl. .................. 544/60; 260/244.4; 544/124; 544/359; 546/304; 546/311; 546/348; 546/193; 546/281
[58] Field of Search .......... 260/296 R, 268 H, 293.69; 544/60, 124, 359

[56] References Cited

PUBLICATIONS

Anger et al, Talanta, vol. 10 (1963), pp. 1302 and 1303.
Jerchel et al, Chem. Ber., vol. 91 (1958), pp. 1266 to 1273.
Klingsberg, Pyridine and Its Derivatives, Interscience, New York, Part II (1961) p. 11 and Part III (1962) p. 11.

*Primary Examiner*—Richard Raymond
*Attorney, Agent, or Firm*—Millen & White

[57] ABSTRACT

A process for the preparation of aminopyridines of the formula

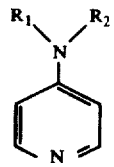

wherein $R_1$ and $R_2$ are identical or different and are hydrogen or lower alkyl or, together with the nitrogen atom to which they are attached, form a 5-, 6-, or 7-membered heterocyclic ring containing up to 2 more hetero atoms, comprises reacting 4-pyridylpyridinium chloride or a salt thereof, at an elevated temperature, with an acid amide of the formula

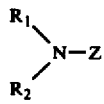

wherein $R_1$ and $R_2$ are as above and Z is —CO—$R_3$ wherein $R_3$ is hydrogen, lower alkyl,

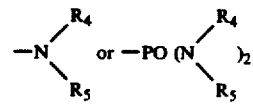

and $R_4$ and $R_5$ are hydrogen or lower alkyl.

33 Claims, No Drawings

PROCESS FOR THE PREPARATION OF AMINOPYRIDINES

This is a continuation or application Ser. No. 677,819 filed Apr. 16, 1976, now abandoned.

BACKGROUND OF THE INVENTION

This invention relates to a novel process for preparing 4-aminopyridines wherein the amino group in the 4-position is present in free or substituted form.

The products of this process are acylating catalysts and are intermediates for the production of active medicinal agents. Typical of medicinally active agents obtained from 4-aminopyridine are esters of steroidal hydroxyl groups e.g. DOS No. 2,137,856 (German Unexamined Laid-Open Application).

In selective or rapid acylation of amines (see, L. M. Litvinenko et al., Chem. Abs. 68, 68325u (1968) and alcohols (see, W. Steglich and G. Hoefle, "Angew. Chemie" 81, 1001 (1969); Tetrahedron Letters 4727 (1970); and Synthesis, 1972, 619), customary acylating catalysts are 4-dialkylaminopyridines, especially 4-dimethylaminopyridine as disclosed in DOS No. 1,958,954 and DOS No. 2,137,856. Known methods for the preparation of substituted 4-aminopyridines are unreliable. Required starting materials can be prepared only be several, expensive steps, for example, amination of 4-chloropyridine with dimethylamine at 150° C. under pressure, L. Pentimalli, Gazz. Chim. Ital. 94, 902 (1964); reaction of silylated 4pyridone with amines, such as pyrrolidine, using acidic catalysis, H. Vorbrueggen, "Angew. Chemie" 84, 348 (1972). or conversion of 4-pyridylphenyl ether by reaction with secondary amines to the corresponding 4-dialkylaminopyridines, D. Jerchel et al., al., "Chem. Ber." 91 1266 (1958).

It has been found in accordance with this invention that 4-aminopyridines can be prepared, in a technically feasible method, simply and directly from readily accessible 4-pyridylpyridinium chloride or a salt thereof, preferably the hydrochloride, by reaction with an easily obtainable acid amide.

SUMMARY OF THE INVENTION

This invention relates to a method of preparing an aminopyridine of Formula I

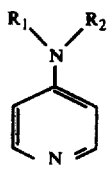

comprising the step of heating a mixture of 4-pyridylpyridinium chloride or a salt thereof, and an acid amide of Formula II

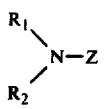

wherein $R_1$ and $R_2$ each are hydrogen or lower alkyl or, collectively with the nitrogen atom to which they are attached, form a 5-, 6-, or 7-membered saturated ring containing 0 to 2 additional hetero atoms, and wherein Z is $-CO-R_3$ and $R_3$ is hydrogen, lower alkyl,

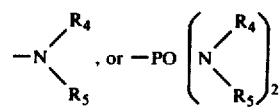

and $R_4$ and $R_5$ are hydrogen, lower alkyl, to produce an aminopyridine of the formula

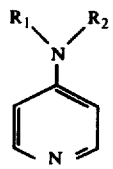

wherein $R_1$ and $R_2$ have the values given above provided that, when $R_3$ is

or

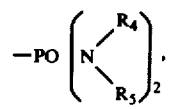

$R_1$ and $R_2$ are the same as $R_4$ and $R_5$.

DETAILED DESCRIPTION

Lower alkyl $R_1$, $R_2$, $R_3$, $R_4$, and $R_5$ are straight-chain and branched. saturated hydrocarbon residues of 1–6 carbon atoms, for example, methyl, ethyl, propyl, isopropyl, butyl, isobutyl, sec.-butyl, pentyl, hexyl, tert.-butyl. Those of 1–4 carbon atoms are preferred. $R_1$ and $R_2$, together with the nitrogen to which they are attached form a 5-, 6-, or 7-membered heterocyclic ring which can contain one or more additional hetero atoms. Preferably the ring contains one further hetero atom, such as N, O or S. Preferably, the heterocyclic substituent is hydrogenated, such as pyrrolidine, piperidine, $N^4$-alkyl piperazine with alkyl as for $R_1$ - $R_5$, morpholine, thiomorpholine, and azepine. Those having 5 or 6 ring members are preferred.

Especially suitable as the acid amides of Formula II are amides of medium strong and weak acids, preferably those of formic acid, acetic acid, carbonic acid, and phosphoric acid.

Examples of suitable acid amides include, but are not limited to dimethylformamide, dimethylacetamide, tetramethylurea, hexamethylphosphoric triamide, N-formylpyrrolidine, N-formylpiperidine, N-formylmorpholine, N-methylformamide, N-methylacetamide, formamide, urea, and acetamide.

Salts of 4-pyridylpyridinium chloride which can be used include salts with strong inorganic or organic acids, e.g. preferably hydrochloric, sulfuric, phosphoric, benzene or p-toluene sulfonic acid, methane sulfonic acid. Also, exemplary of salts which can be used are sulfate, hydrogen sulfate and hydrochloride. The hydrochloride is preferred.

The preferred processes of this invention are those for preparing compounds of Formula I wherein:

(a) $R_1$ and $R_2$ each are hydrogen;
(b) $R_1$ and $R_2$ each are alkyl of 1–6 carbon atoms;
(c) $R_1$ and $R_2$ together with the N to which they are attached form a 5–7-membered saturated heterocyclic ring containing 0 to 2 additional hetero atoms;
(d) $R_1$ and $R_2$ collectively are tetramethylene;
(e) $R_1$ and $R_2$ collectively are pentamethylene;
(f) $R_1$ and $R_2$ collectively are hexamethylene;
(g) $R_1$ and $R_2$ collectively are $-CH_2CH_2OCH_2CH_2-$;
(h) $R_1$ and $R_2$ collectively are $-CH_2CH_2SCH_2CH_2-$
(i) $R_1$ and $R_2$ collectively are

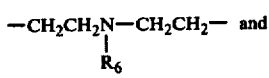

$R_6$ is hydrogen or alkyl of 1–6 carbon atoms.

(j) Z in Formula II is $-COR_3$ and $R_3$ is hydrogen or alkyl of 1–6 carbon atoms, including (a) - (i);
(k) Z is $-COR_3$, $R_3$ is

and $R_4$ and $R_5$ are hydrogen or alkyl of 1–8 carbon atoms, including (a) - (i); and
(l) Z is $-COR_3$ and $R_3$ is

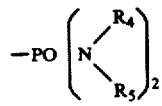

and $R_4$ and $R_5$ are hydrogen or alkyl or 1–6 carbon atoms, including (a)-(i).

The preparation of preferred compounds of this invention, wherein $R_1$ and $R_2$ collectively form a heterocyclic ring, it will be understood that heterocyclic rings substituted by alkyl of 1 - 6 carbon atoms, aralalkyl of a total of 10 carbon atoms and aryl groups, e.g. phenyl, naphthyl, and equivalents thereof, are within the scope of the invention.

The acid amide of Formula II used normally also serves simultaneously as solvent for the reaction, but an inert organic solvent can be added to the reaction mixture as a diluent and/or solubilizer. If the acid amide is present in solid form, the reaction takes place in the melt or in the presence of an inert organic solvent. The reactants can be used in molar amounts, but preferably the acid amide is used in excess, preferably 1–5 equivalents. The reaction takes place at an elevated temperature, e.g., at the boiling temperature of the acid amide or solvent employed, preferably at 120–220° C.

To attain optimum yields of the desired product, it is advantageous to remove the pyridine formed during the reaction continuously from the reaction mixture, for example, by a short distillation column. The reaction is terminated when about 1 mole of thus-formed pyridine has been distilled off. The product of this process is isolated in the usual way, for example, by adding an excess of an aqueous alkali, preferably 2–3 moles, to the reaction mixture, and separating the product by steam distillation or exhaustive extraction, e.g., with methylene chloride.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

229 g. (1 mole) of crude 4-pyridylpyridinium chloride hydrochloride (Org. Synthesis Coll., V, 977) was dissolved in 146.2 g. (2 moles) of dimethylformamide at about 140–150° C. Under agitation, the reaction mixture was heated for 2 hours at a bath temperature of 180° C., thus removing by distillation 90 ml. of crude pyridine (b.p. 111–122° C.). The dark residue was allowed to stand with 100 g. of NaOH in 1 liter of $H_2O$, and then the mixture was filtered off from the dark, insoluble residue, and the residue and solution were extracted exhaustively with methylene chloride. After drying the methylene chloride extracts ($Na_2SO_4$) and treatment with a small amount of carbon, 68.3 g. (56%) of crude 4-dimethylaminopyridine was obtained, melting at 112–113° C. after recrystallization from diisopropyl ether.

EXAMPLE 2

The procedure of Example 1 was followed, except that 174 g. (2 moles) of dimethylacetamide was utilized in place of 146.2 g. (2 moles) of dimethylformamide. After heating the reaction mixture and working same up analogously, the yield was 74.2 g. (61%) of 4-dimethylaminopyridine.

EXAMPLE 3

The method of Example 1 was employed, except for using 2–3 moles of tetramethylurea instead of the dimethylformamide. Yield: 56% of 4-dimethylaminopyridine, m.p. 112–113° C.

EXAMPLE 4

229 g. (1 mole) of 4-pyridylpyridinium chloride hydrochloride in 179 g. (1 mole) of hexamethylphosphoric triamide was heated under agitation for 1 hour to 220° C. while the pyridine is being distilled off (40 ml.). After cooling, the residue was taken up in 500 ml. of $H_2O$ and heated for 1.5 hours on a steam bath. The slightly acidic solution (ph about 5) was filtered by way of a soft, folded filter, and the insoluble brown proportion was washed twice with respectively 100 ml of 2N HCl. The combined filtrate was made strongly alkaline with about 200 ml. of 40% KOH and was extracted exhaustively with methylene chloride. After drying ($Na_2SO_4$) and evaporation, the thus-remaining viscous oil (107.59 g.) was extracted with 1.5 liter of diisopropyl ether and treated with a small amount of carbon. From the filtrate there crystallized, at 4° C., 65.79 g. (53.8%) of pure 4-dimethylaminopyridine, m.p. 112–113° C.

EXAMPLE 5

Under agitation, 22.9 g. (0.1 mole) of crude 4-pyridylpyridinium chloride hydrochloride in 30 g. (0.3 mole) of N-formylpyrrolidine was heated for 3.5 hours to 180°

C., while pyridine was distilled off. The dark residue was allowed to stand overnight with 250 ml. of 2N NaOH and extracted exhaustively with methylene chloride. The extracts yielded, after drying (Na₂SO₄), carbon treatment, and evaporation, 11.5 g. of a brown oil which was repeatedly extracted with methylene chloride/hexane. The extracts were recrystallized from hexane, thus obtaining 8.95 g. (60.5%) of 4-pyrrolidinopyridine, m.p. 55–57° C.

EXAMPLE 6

22.9 g. (0.1 mole) of crude 4-pyridylpyridinium chloride hydrochloride was heated in 33.9 g. (0.3 mole) of N-formylpiperidine and then worked up as described in Example 3; recrystallization from ligroin yielded 4.35 g. (58%) of 4-piperidinopyridine, m.p. 81° C.

EXAMPLE 7

With complete analogy to Examples 5 and 6, the reaction of 4-pyridylpyridinium chloride hydrochloride with N-formylmorpholine produced, in a 59% yield, 4-morpholinopyridine, m.p. 93–95° C. (from ligroin).

EXAMPLE 8

344 g. (1.5 moles) of crude 4-pyridylpyridinium chloride hydrochloride was heated under agitation in 241 g. (4.2 moles) of N-methylformamide for 2.5 hours to 190° C., removing 120 ml. of pyridine by distillation. After cooling, the black residue was allowed to stand in 100 ml. of 3N NaOH for 16 hours and then exhaustively extracted with methylene chloride. After drying (Na₂SO₄), treatment with a small amount of carbon, and evaporation, the yield was 85 g. (52.5%) of crude, yellowish, crystalline 4-methylaminopyridine, melting at 121–124° C. after recrystallization from toluene.

EXAMPLE 5

The procedure of Example 8 was followed, except that N-methylacetamide was used in place of N-methylformamide. Yield: 53% of 4-methylaminopyridine, m.p. 121–124° C.

EXAMPLE 10

115 g. (0.5 mole) of 4-pyridylpyridinium chloride hydrochloride was heated in 100 ml. (2.5 moles) of formamide under agitation to 150° C., resulting in a complete solution of all compounds, and the solution was heated gently and gradually to 180° C. (the solution is very frothy!), while pyridine was distilled off. After one hour at 180° C., the reaction mixture was cooled, heated for 3 hours on a steam bath with a solution of 120 g. of NaOH in 500 ml. of H₂G, and filtered over glass wool. The insoluble residue was washed with methylene chloride and the black, alkaline filtrate was extracted continuously with methylene chloride, yielding 24.9 g. (53%) of 4-aminopyridine, m.p. 156–158° C.

EXAMPLE 11

This example was carried out analogously to Example 10 except that acetamide was employed instead of formamide. Yield: 58% of 4-aminopyridine.

EXAMPLE 12

The procedure was followed as described in Example 10, reacting 4-pyridylpyridinium chloride hydrochloride with 3–5 equivalents of urea. Likewise, with vigorous foaming, 4-aminopyridine was obtained at 160–180° C. in a yield of 63%, m.p. 156–158° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of aminopyridines which comprises the step of reacting, at about 120–220° C., 4-pyridyl-pyridinium chloride or a salt thereof with an acid amide of the formula

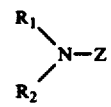

wherein $R_1$ and $R_2$ each are hydrogen or lower alkyl or, collectively with the nitrogen atom to which they are attached, form a 5-, 6-, or 7-membered saturated heterocyclic ring containing 0 to 2 additional hetero atoms, selected from the group consisting of N, O and S, and wherein Z is —CO—$R_3$ and $R_3$ is hydrogen, lower alkyl,

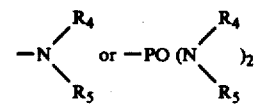

and $R_4$ and $R_5$ are hydrogen, or lower alkyl, to produce pyridine and an aminopyridine of the formula

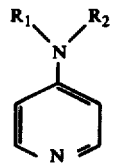

wherein $R_1$ and $R_2$ have the values given above.

2. The process of claim 1, wherein $R_1$ and $R_2$ each are hydrogen.

3. The process of claim 1, wherein $R_1$ and $R_2$ each are alkyl of 1–6 carbon atoms.

4. The process of claim 1, wherein $R_1$ and $R_2$ together with the nitrogen atom to which they are attached form a heterocyclic ring as defined therein.

5. The process of claim 1, wherein $R_1$ and $R_2$ collectively are tetramethylene.

6. The process of claim 1, wherein $R_1$ and $R_2$ collectively are pentamethylene.

7. The process of claim 1, wherein $R_1$ and $R_2$ collectively are hexamethylene.

8. The process of claim 1, wherein $R_1$ and $R_2$ collectively are —$CH_2CH_2OCH_2CH_2$—.

9. The process of claim 1, wherein $R_1$ and $R_2$ collectively are —$CH_2CH_2SCH_2CH_2$—.

10. The process of claim 1, wherein $R_1$ and $R_2$ collectively are

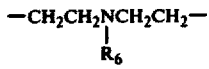

and R$_6$ is hydrogen or alkyl of 1–6 carbon atoms.

11. The process of clain 1, wherein Z is —COR$_3$ and R$_3$ is hydrogen or alkyl of 1–6 carbon atoms.

12. The process of claim 1, wherein Z is —COR$_3$, R$_3$ is

and R$_4$ and R$_5$ are hydrogen or alkyl of 1–6 carbon atoms.

13. The process of claim 1, wherein Z is —COR$_3$, R$_3$ is

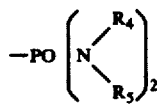

and R$_4$ and R$_5$ are hydrogen or alkyl of 1–6 carbon atoms.

14. The process of claim 1, wherein the acid amide is the reaction solvent.

15. The process of claim 1, wherein the reaction is conducted in the fused acid amide.

16. The process of claim 1, wherein 4-pyridyl-pyridinium chloride hydrochloride is employed.

17. The process of claim 1, wherein the pyridine produced by the reaction is removed continuously from the reaction mixture.

18. The process of claim 1, which further comprises the step of isolating the thus-produced aminopyridine.

19. The process of claim 18, wherein the isolating step comprises adding excess aqueous alkali to the reaction mixture prior to physical separation of the product.

20. The process of claim 18, which further comprises separating the isolated product by steam distillation or exhaustive extraction.

21. The process of claim 1, wherein the reacting step is conducted for at least one hour.

22. The process of claim 1, wherein the reacting step is conducted for 1–3.5 hours.

23. The process of claim 1, wherein the reaction temperature is 180–220° C.

24. The process of claim 1, wherein the reaction temperature is 140–220° C.

25. The process of claim 17, wherein the pyridine by-product is continuously removed from the reaction mixture during the reaction by distillation.

26. The process of claim 25, wherein the pyridine by-product is removed by column distillation.

27. The process of claim 1, wherein the starting reaction medium consists essentially of 4-pyridyl-pyridinium chloride and one acid amide.

28. The process of claim 11, wherein the starting reaction medium consists essentially of 4-pyridyl-pyridinium chloride and one acid amide.

29. The process of claim 12, wherein the starting reaction medium consists essentially of 4-pyridyl-pyridinium chloride and one acid amide.

30. The process of claim 28, wherein the starting reaction medium consists essentially of 4-pyridyl-pyridinium chloride and dimethylformamide.

31. The process of claim 29, wherein the starting reaction medium consists essentially of 4-pyridyl-pyridinium chloride and urea.

32. The process of claim 1, whereby a substantial amount of amino pyridine product is produced.

33. The process of claim 1, wherein the reaction is conducted until more than half of the 4-pyridyl-pyridinium chloride is converted to aminopyridine product.